US00PP15584P3

(12) United States Plant Patent
Redman

(10) Patent No.: US PP15,584 P3
(45) Date of Patent: Feb. 22, 2005

(54) ***CHRYSANTHEMUM* PLANT NAMED 'VAMP TIME SALMON'**

(50) Latin Name: *Chrysanthemum morifolium*
Varietal Denomination: Vamp Time Salmon

(75) Inventor: Ruth Redman, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 4 days.

(21) Appl. No.: 10/365,159

(22) Filed: Feb. 11, 2003

(65) Prior Publication Data

US 2004/0158903 P1 Aug. 12, 2004

(51) Int. Cl.[7] ..... A01H 5/00
(52) U.S. Cl. ..... Plt./291
(58) Field of Search ..... Plt./291, 290, 287

(56) References Cited

U.S. PATENT DOCUMENTS

PP8,573 P 2/1994 Wain

OTHER PUBLICATIONS

Brummitt, 1997. The Garden, Horticultural Science: *Chrysanthemum* once again, pp. 662–663.*

2001 Ficor catalog, listing the variety 'Vamp Time.' See, e.g., p. 4.

2002 Ficor catalog, listing the variety 'Vamp Time.' See, e.g., p. 4.

* cited by examiner

*Primary Examiner*—Anne Marie Grunberg
*Assistant Examiner*—June Hwu
(74) *Attorney, Agent, or Firm*—Howrey Simon Arnold & White LLP

(57) ABSTRACT

A new variety of *Chrysanthemum* plant named 'Vamp Time Salmon,' having a good uniform canopy of salmon decorative flowers. The new variety has a medium vigour, free branching, with a uniform spreading habit and good foliage presentation.

1 Drawing Sheet

Latin name of the genus and species: Botanical classification: *Chrysanthemum morifolium.*

Variety denomination: The new *Chrysanthemum* variety denomination is 'Vamp Time Salmon.'

BACKGROUND OF THE INVENTION

The present invention comprises a new and distinct cultivar of *Chrysanthemum* botanically known as *Chrysanthemum morifolium,* and referred to by the cultivar name 'Vamp Time Salmon.' 'Vamp Time Salmon,' identified as 20544-3, originated from a naturally occurring whole plant mutation grown in a controlled planting of the unpatented variety 'Vamp Time,' in Chichester, West Sussex, United Kingdom. The new variety 'Vamp Time Salmon' has been asexually reproduced by vegetative cuttings in Chichester, West Sussex, United Kingdom and the distinguishing characteristics are retained through successive generations of asexual reproduction.

BRIEF SUMMARY OF THE INVENTION

'Vamp Time Salmon' is a pot type of *Chrysanthemum* plant variety having salmon decorative flowers with a domed capitulum form.

Comparison with Parent

Plants of the new *Chrysanthemum* variety 'Vamp Time Salmon' are similar to the parent 'Vamp Time' in plant habitat and growth rate. In side-by-side comparisons in Chichester, West Sussex, United Kingdom, under commercial practice, plants of the new *Chrysanthemum* variety 'Vamp Time Salmon' compared to plants of the parent 'Vamp Time' in the following characteristics.

1. The new variety 'Vamp Time Salmon' produces salmon decorative flowers whereas the parent 'Vamp Time' produces light pink flowers.
2. Plants of the new variety 'Vamp Time Salmon' have similar inflorescence to plants of the parent 'Vamp Time.'

Comparison with Other Varieties

Plants of the new *Chrysanthemum* variety 'Vamp Time Salmon' are similar to 'Wain's Pink Lady,' (U.S. Plant Pat. No. 8,573), in plant habitat and growth rate. However, in side-by-side comparisons in Chichester, West Sussex, United Kingdom, under commercial practice, plants of the new *Chrysanthemum* variety 'Vamp Time Salmon' differed from plants of 'Wain's Pink Lady' in the following characteristics.

1. The new variety 'Vamp Time Salmon' produces salmon decorative flowers whereas 'Wain's Pink Lady' produces pink decorative flowers.
2. Plants of the new variety 'Vamp Time Salmon' have larger and taller inflorescence than plants of 'Wain's Pink Lady.'

BRIEF DESCRIPTION OF ILLUSTRATION

Typical specimens of the plant and flowers for the new *Chrysanthemum* variety 'Vamp Time Salmon' are shown in the accompanying digital photograph. The colors shown are as true as possible within the usual limits of this kind of illustration.

FIG. 1 is a whole plant view of the new variety 'Vamp Time Salmon' grown in a pot. The plant shown in the illustration is 54 day from the commencement of Short Days.

DETAILED BOTANICAL DESCRIPTION

The following description of the new *Chrysanthemum* variety 'Vamp Time Salmon' is of plants grown in a greenhouse in Chichester, West Sussex, United Kingdom in the month of May. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5000 to 6000 foot candles. The plants respond well to the use of growth retardant, such as B9 treatment at about 2 g per liter. To produce a commercial product the plants may be pinched once with the center bud removed. The typical container size for commercial growth is 1 liter. It has been observed that the shelf life of the new variety is about 28 days with a response time of about 7.5 weeks. The new variety is suitable for growth in a temperature range of 15° C. to 25° C.

The new variety may be produced as a spray. The following description is with respect to a plant produced as pot *Chrysanthemum.* In the description of this new *Chrysanthemum* variety, color values have been taken from The Royal Horticultural Society Colour Chart (R.H.S.C.C.).

Plant

Plant type: Pot.
Habit: Upright and free branching.
Height: 20 cm.
Width: 32 cm.
Branching characteristics: Upright and free branching.
Length of lateral branches: 12 cm.
Number of breaks from pinch: 4.
Stem color: 138B.
Response time: 52 days.
Vigor: Medium.
Shelf life: 28 days.
Disease/pest (susceptibility/resistance observed): None observed to date.
Growth retardant type and treatment: 3 applications of 2.5 gm/liter B9 @2, 21 and 28 days after sticking unrooted cuttings.

The plants were grown for 2 weeks in Long Day conditions (20 hours of light) and then transferred to Short Day conditions (13 hours of dark).

Propagation:
- *Type.*—Vegetative propagation via stem cuttings.
- *Time to rooting.*—14 days with soil temperatures of 18° C.
- *Rooting habit.*—After 7 days the first roots emerge and form root primordia. In 14 Long Days a complete root system is developed.

Foliage

Number of leaves per lateral branch: 9.
Compound or single: Single.
Arrangement of leaves: Alternate.
- *Shape of leaf.*—Typically 5 lobed.
- *Size of leaf.*—Width (cm): 4.5 Length (cm): 7.
- *Leaf apex.*—Acute.
- *Base.*—Cordate.
- *Attachment.*—Petioled.
- *Aspect.*—Slightly undulating.
- *Margin.*—Lobed.
- *Surface characteristics.*—Top: slightly pubescent. Bottom: pubescent.

Petiole:
- *Color.*—138A.
- *Length.*—1.3 cm.
- *Diameter.*—0.2 cm.
- *Surface.*—Slightly pubescent.

Venation: Net prominent mid vein at underside.
- *Color.*—Upper side: near 147C. Under side: near 147C.

Color: Mature Leaf, upper side: near 137A; under side: near 137C. Young Leaf, upper side: near 147A; under side: near 137C.

Flower

Flower appearance: Matte.
Flower type: Decorative.
Flower form: Domed.
Flower shape: Round.
Flowering habit: Domed capitulum.
Number of blossoms per branch: 4.
Inflorescence form: Cyme.
- *Depth of fully expanded blossoms.*—1.5 cm.
- *Diameter of fully expanded blossoms.*—9 cm.

Phyllaries:
- *Number.*—13.
- *Color.*—Near 138A.
- *Length.*—0.7 cm.
- *Width.*—0.4 cm.
- *Texture/appearance.*—Pubescent.

Peduncle: Peduncle length is shortest at the terminal flower and progressively longer moving down the stem.
- *Length.*—8.5 cm (average).
- *Diameter.*—0.6 cm.
- *Color.*—Near 138B.
- *Surface.*—Slightly pubescent.
- *Habit.*—Slightly curving.
- *Strength.*—Moderately strong.

Pedicel:
- *Length.*—Terminal: 3 cm; lateral: 3.5 cm.
- *Diameter.*—0.3 cm.
- *Color.*—Near 138B.
- *Surface.*—Slightly pubescent.
- *Habit.*—Slightly curving.
- *Strength.*—Moderately strong.

Ray florets:
- *Form/shape.*—Straight with parallel edges to the central mid vein.
- *Texture/appearance.*—Matte.
- *Number per flower.*—95.
- *Length.*—4 cm; Width 1.3 cm.
- *Apex.*—Dentate.
- *Base.*—Tapered.
- *Margin.*—Entire.

Disc florets:
*Form/shape.*—Cylindric.
*Texture/appearance.*—Shiny.
*Number per flower.*—14.
*Length.*—0.5 cm; Width: 0.1 cm.
*Diameter of disc.*—0.3 cm.
Fragrance: None.
Flower bud (at onset of color):
*Length.*—1.8 cm.
*Diameter.*—1.5 cm.
*Form/shape.*—Spherical.
General flower color:
1. *Ray florets, upper side.*—51D. Immature: near 51D. Mature: near 51D. Older/Fading: near 50D.
2. *Ray florets, under side.*—36B. Immature: near 37C. Mature: near 36B. Older/Fading: near 36D.
3. *Disc florets.*—Immature: near 145B. Mature: near 145B. Older/Fading: near 145C.
4. *Bud.*—51C.

Flower progression with age: Flower form does not change but there is a slight color fading with age.
Lastingness of blooms: About 28 days.

Reproductive Organs

Gynoecium: Present on Ray and Disc florets.
Ray florets per individual flower:
*Pistil number.*—95.
*Stigma color.*—Near 3A.
*Stigma shape.*—Forked.
*Style color.*—Near 154B.
*Style length.*—0.4 cm.
Disc florets per individual flower:
*Pistil number.*—14.
*Stigma color.*—Near 3A.
*Stigma shape.*—Forked.
*Style color.*—Near 154B.
*Style length.*—0.4 cm.
Androecium: Not observed.
Fruit and Seeds: None observed.

What is claimed is:

1. A new and distinct variety of *Chrysanthemum* plant, substantially as described and illustrated herein.

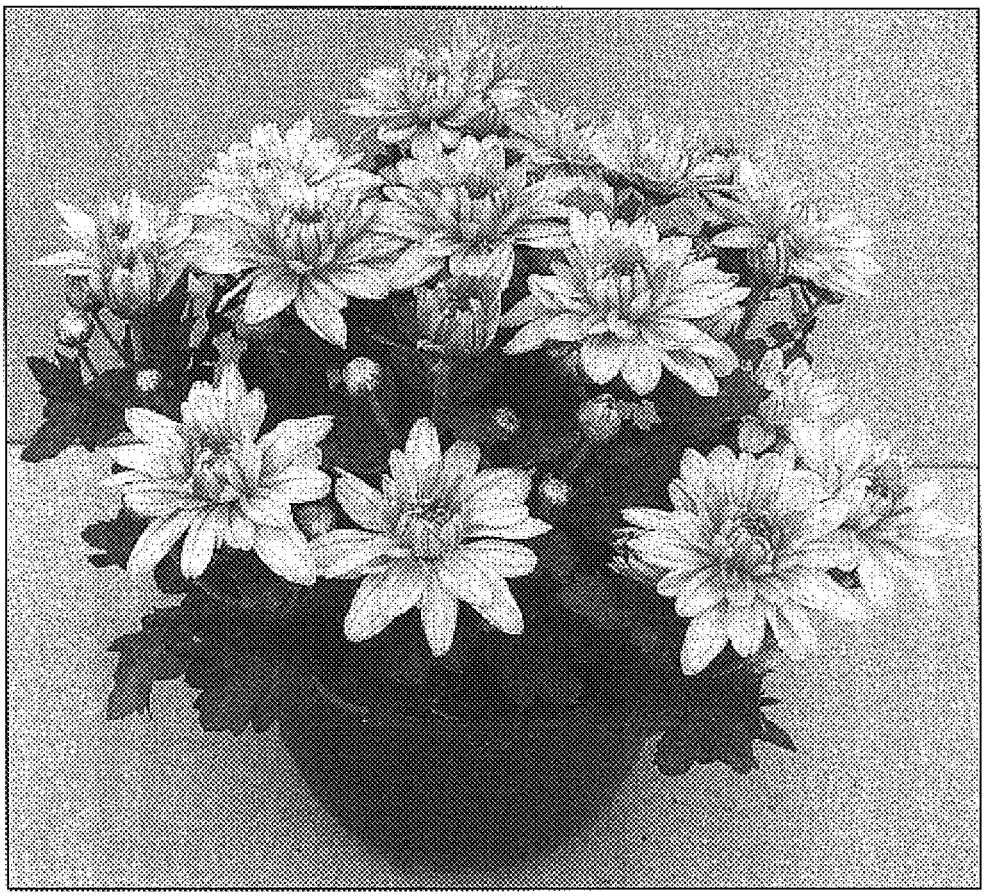

* * * * *